United States Patent [19]
Aguiar

[11] 4,227,517
[45] Oct. 14, 1980

[54] CAST CUTTING SYSTEM
[76] Inventor: Robert H. Aguiar, 4510 Elderberry Dr., Orlando, Fla. 32809
[21] Appl. No.: 7,436
[22] Filed: Jan. 29, 1979
[51] Int. Cl.³ .............................................. A61F 5/04
[52] U.S. Cl. .................................... 128/91 A; 30/116
[58] Field of Search .............. 128/91 A, 91 R, 83; 30/116, 123, 124

[56] References Cited
U.S. PATENT DOCUMENTS
2,746,452 5/1956 Saylors .............................. 128/91 A
3,867,931 2/1975 Babka ................................ 128/91 A FOREIGN PATENT DOCUMENTS
731182 6/1955 United Kingdom .................. 128/91 A

*Primary Examiner*—John D. Yasko
*Attorney, Agent, or Firm*—Duckworth, Hobby & Allen

[57] ABSTRACT

System and apparatus for removing a casted wall from a human appendage includes a strand embedded laterally through the wall at an inner surface thereof and adjacent the human appendage, and a take-up roller for severing the wall by drawing the strand into a cutting angle adjacent the inner surface and then through the wall, and further including a guide exterior of the wall and having a guide surface about which the strand is drawn. The guide surface is disposed substantially away from the cutting angle along the direction of travel of the take-up roller and the guide, whereby the strand is drawn through the wall and it is at a substantially acute angle of less than 60 degrees.

12 Claims, 2 Drawing Figures

CAST CUTTING SYSTEM

BACKGROUND OF THE INVENTION

1. Field of the Invention

The present invention relates to apparatus and processes for removing and severing casted material, and in particular relates to such apparatus and processes which are designed to remove molded casts from human appendages, such as arms and legs.

2. Description of the Prior Art

Molded casts of a plaster-like material are commonly used to set broken human limbs (i.e. arms and legs) in a position which permits the bone structure to heal. After the healing process is completed, it is of course necessary to remove the casted material from the human appendage. To this end, numerous hand tools have been devised for permitting the casted material to be cut away from the arm or leg, but such tool arrangements provide an unnecessary risk of injury to the patient.

There have also been suggestions in the prior art to provide an embedded strand in the casted material adjacent the inner surface of the casted wall, and further including means for withdrawing the strand through the casted material to sever the wall of the cast to thereby facilitate removal. See, for example, U.S. Pat. No. 1,967,888 to Kearsley, which discloses a simple dual rollar arrangement employing such an embedded strand which is wound about the dual rollers to permit severing the cast. A similar arrangement is taught in U. S. Pat. No. 3,867,931 to Babka.

In U.S. Pat. No. 3,085,969, Cook et al discloses a separable plaster cast employing a conventional zipper arrangement for purposes of removing the cast.

Of particular interest, Saylors in U.S. Pat. No. 2,746,452, discloses a machine having a guide roller for permitting the strand to be drawn substantially directly upward to the cast material to sever the cast wall for removal. The apparatus disclosed by Saylors includes a hand crank and a guide roller, the guide roller making the only contact with the casted wall.

Other prior art of interest includes U.S. Pat. No. 4,041,941 to Driver, and U.S. Pat. No. 2,342,695 to Rinaldy.

SUMMARY OF THE INVENTION

The present invention contemplates a system and associated apparatus for removing a casted wall from a human appendage, and includes a strand of material embedded laterally through the wall at the inner surface thereof which is adjacent to the human appendage, and means for severing the wall by drawing the strand into a cutting angle adjacent the inner surface and then through the wall, the severing means including a guide exterior of the wall and having a guide surface about which the strand is drawn. The guide surface is disposed substantially away from the cutting angle along the direction of travel of the severing means, whereby the strand is drawn through the wall at a substantially acute angle of less than 60 degrees.

In order to maintain the angular relationship between the guide wall and the cutting angle of the strand, in the manner described above, the severing means further includes a low friction skid having a flat surface for contacting the outer surface of the casted wall and maintaining that angular relationship during movement of the severing means along the direction of travel. Preferably, the skid includes a slot therein adapted to receive the strand while being drawn upward to the casted wall by the severing means whereby extraneous matter may be removed from the strand at the slot in the skid.

Further, in accordance with the present invention, the severing means includes a housing having a handle portion which extends substantially parallel with the casted wall, thereby permitting the entire severing assembly to be pushed laterally in a direction parallel with the wall being severed, with one-hand operation.

THE DRAWING

DETAILED DESCRIPTION

A preferred embodiment of the system and apparatus of the present invention will now be described with reference to FIGS. 1 and 2.

Figure 1:
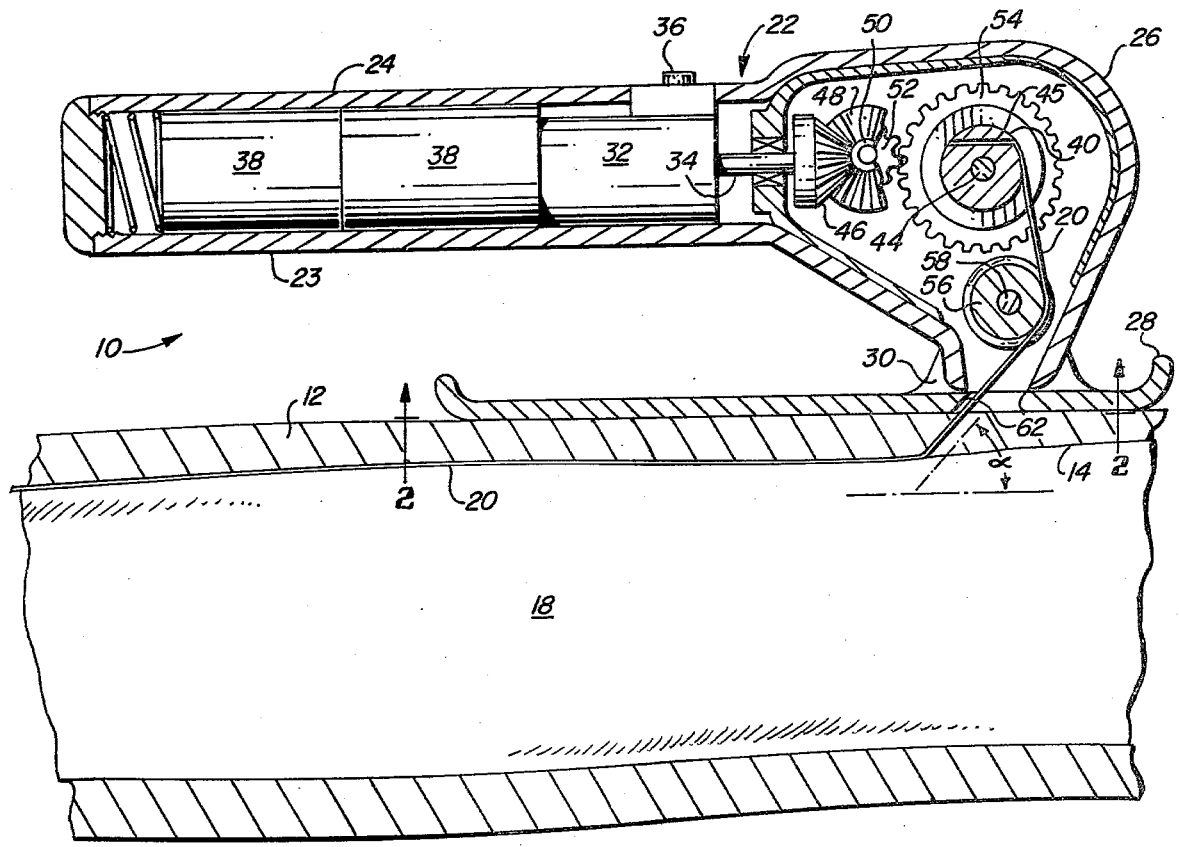
FIG. 1 is a cross sectioned side view of apparatus in accordance with the present invention, shown utilized in conjunction with a casted wall which is being cut.

Noting FIG. 1, the cast cutting apparatus of the present invention is referred to generally with the reference numeral 10. The cutting device 10 is adapted to sever a casted wall 12 of a conventional plaster material, and having an inner surface 14 and an outer surface 16. The casted wall 12 is molded about a human appendage, such as an arm or a leg, which is denoted by the reference numeral 18.

In accordance with the present invention, a non-toxic stand 20, which is preferably nylon or a similar monofilament material, but which may comprise steel wire, is disposed adjacent the lower surface 14 in a conventional manner to leave one extremity of the strand free.

Again referring to FIG. 1, the cast cutter 10 includes a housing 22 having a handle portion 23 which is formed as a cylinder extending substantially parallel with the casted wall 12. The housing 22 includes a power unit 24 located within the handle 23, and a roller unit 26 positioned within the forward portion of the housing 22. The cast cutter 10 further includes a skid 28 comprising a substantially flat surface having curved extremities and which is joined to the roller unit 26 of the housing 22 by a brace 30.

The cast cutter 10 is provided with a motor 32 located within the handle 23, the motor having an associated drive shaft 34. The motor further includes a three position forward-off-reverse switch 36 which permits operation of the motor 32 from outside the housing 22. The motor 32 may be powered by a conventional alternating current line voltage, or alternatively may be powered by onboard batteries 38 located within the handle portion 23. As shown in FIG. 1, the handle 23 is shaped to permit one-hand operation with the switch 36 controlled by the thumb. The switch 36 is in "off" position when centered, and includes springs 35 and 37 which return the switch to the off position when thumb pressure is released.

Referring to the forward, roller unit 26 of the housing 22, the roller unit includes a take-up roller 40 having a slot 42 therein, the take-up roller being fixed on an axle 44, and being provided with an aperture 45 through which the free extremity of the strand 20 is extended in order to draw the strand outward by rotation of the take-up roller 40. A first cone gear 46 is coupled to the drive shaft 34 in a conventional manner. A second cone gear is fixed on a second axle 50, and is meshed with the first cone gear 46 to be driven thereby. A shaft gear 52 (FIG. 2) is fixed on the axle 50 and meshes with a reduction gear 54 fixed on the axle 44, in order to rotate the roller 40.

Figure 2:
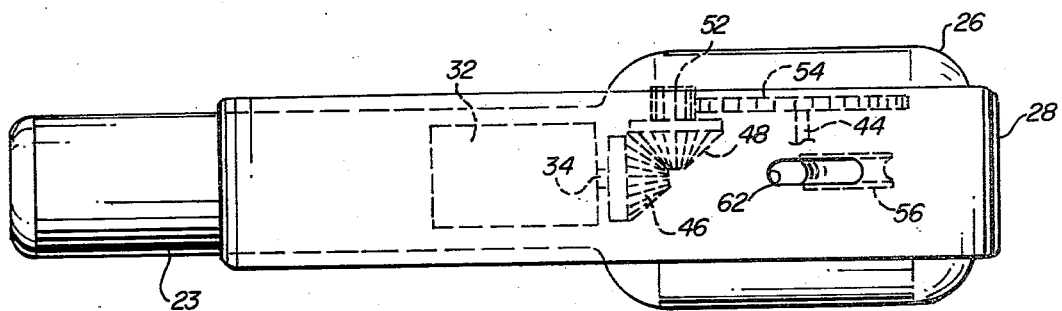
FIG. 2 is a side view of a portion of the apparatus shown in FIG. 1, taken along the line 2—2.

Noting both FIGS. 1 and 2, a guide roller 56 is freely rotatable on an axle 58, and has a groove 60 therein to engage the strand 20, as the strand is drawn through the wall, and then through a slot in the skid, through an aperture 62 in the lower extremity of the roller unit portion 26 of the housing 22, thence across the guide roller 56 and about the take-up roller 40.

As has been indicated previously, the cast cutter 10 is operated by initially extending the free extremity of the strand 20 across the guide roller 56 and into the aperture 45 associated with the take-up roller 40. The switch 36 is then operated into the forward position, causing the motor 32 to rotate the drive shaft 34, causing the take-up roller 40 to turn in the desired manner. As the take-up roller 40 rotates, the strand 20 is drawn through the slot skid 28, through the aperture 62 in the bottom of the roller unit 26 of the housing 22, across the groove 60 in the guide roller 56 and thence across the take-up roller 40. It will be noted that both the slot in the skid 28 and the groove 60 in the guide 56, as well as the slot in the take-up roller 40 remove unwanted cast material which is inadvertently drawn into the housing 22 with the strand.

In accordance with a particular aspect of the present invention, the guide roller 56 is positioned well forward of the slot in the skid 28, in order that the strand 20 forms a substantially acute angle, preferably of less than 60 degrees, with respect to the lower surface 14 of the casted wall 12. This is represented by the angle alpha in FIG. 1. In this manner, the angle of attack of the strand 20 across the casted wall to be cut is maximized with respect to cutting efficiency.

After the strand has been removed, the motor is operated in the reverse direction, to unwind the strand.

I claim:

1. A system for removing a casted wall from a human appendage, comprising:
    a strand including an outer, non-metallic and non-toxic material embedded laterally through said wall at an inner surface thereof which is adjacent the human appendage;
    means for severing said wall by drawing said strand into a cutting angle adjacent said inner surface and then through said wall, said severing means including a guide exterior of said wall and having a guide surface about which said strand is drawn, said guide surface being disposed substantially away from said cutting angle along the direction of travel of said severing means, whereby said strand is drawn through said wall at a substantially acute angle of less than 60 degrees said severing means comprising:
    (a) a low-friction skid having a flat surface with a slot therein with said strand drawn through said slot, said flat surface of said skid for contacting the outer surface of said wall and maintaining said angular relationship with said strand during movement of said skid along said direction of travel, and whereby extraneous material may be removed from said strand during passage through said slot, with said skid positioned between said guide and said outer surface;
    (b) a roller engaging said strand with means for rotating said roller for drawing said strand through said wall; and
    (c) a motor having a drive shaft, and a gear drive coupled between said drive shaft and said roller.

2. The system recited in claim 1 wherein said gear drive includes gear reduction means.

3. Apparatus for cutting a casted wall by drawing an embedded strand through said wall, said apparatus comprising:
    a low-friction skid having a flat surface for sliding along the outer surface of said wall;
    a roller carried by said skid for engaging an extremity of said strand and drawing said strand through said wall;
    a motor carried by said skid and coupled for driving said roller; and
    means for guiding said strand onto said roller.

4. Apparatus recited in claim 3 wherein said guide means further includes means for drawing said strand through said wall at an acute angle of less than 60 degrees with respect to said wall.

5. The apparatus recited in claim 4 wherein said skid further includes a slot, with said strand drawn therethrough, whereby extraneous material may be removed from said strand.

6. The apparatus recited in claim 4 wherein said severing means further includes a roller having a slot dimensioned approximately to that of the diameter of said strand, whereby extraneous matter is wiped free of said strand in said slot.

7. The apparatus recited in claim 2 wherein said roller further includes a hole therein for engaging said extremity of said strand.

8. A system for removing a casted wall from a human appendage, comprising:
    a strand of a non-metallic, non-toxic material extending lengthwise along the inner surface of said casted wall;
    a skid having a flat surface for sliding along the outer surface of said wall;
    a housing carried by said skid; and
    means including a guide and a motor carried within said housing for drawing said strand through said wall into said housing to thereby sever said cast.

9. The system recited in claim 8 wherein said drawing means further includes means for drawing said strand through said wall at an acute angle of less than 60 degrees with respect to said wall.

10. The system recited in claim 8 wherein said drawing means further includes a take-up roller having an aperture therein for receiving said strand.

11. The system recited in claim 8 wherein said housing comprises a handle extending parallel with said wall in said direction of travel, to facilitate movement of said drawing means in said direction of travel.

12. The system recited in claim 11, further comprising a spring-loaded switch mounted on said handle for operating said drawing means only when operator pressure is applied to said switch.

* * * * *